United States Patent [19]

Maltz

[11] Patent Number: 4,459,289

[45] Date of Patent: Jul. 10, 1984

[54] COPOLYMERS HAVING BACTERICIDAL ACTIVITY, PROCESS FOR THE PREPARATION THEREOF AND PHARMACEUTICAL COMPOSITIONS THEREFROM

[75] Inventor: Javier E. Maltz, Buenos Aires, Argentina

[73] Assignee: Texcontor - Anstalt, Vaduz, Liechtenstein

[21] Appl. No.: 336,964

[22] Filed: Jan. 4, 1982

Related U.S. Application Data

[63] Continuation-in-part of Ser. No. 201,297, Oct. 27, 1980, abandoned.

[30] Foreign Application Priority Data

Jun. 18, 1980 [IT] Italy ................. 22851 A/80

[51] Int. Cl.³ ............... A61K 31/73; A61K 7/035
[52] U.S. Cl. ................. 424/180; 424/DIG. 2; 424/DIG. 4; 424/49; 424/69; 424/78; 424/361; 424/362
[58] Field of Search ............ 424/180, 361, 362, 78, 424/DIG. 2, DIG. 4

[56] References Cited

U.S. PATENT DOCUMENTS

| Re. 26,510 | 12/1968 | Mazzarella et al. | 260/17.4 ST |
|---|---|---|---|
| 3,567,420 | 3/1971 | Legator et al. | 424/78 |
| 4,035,146 | 7/1977 | Brenner et al. | 424/362 |
| 4,080,346 | 3/1978 | Bedell | 260/17.46 C |
| 4,131,576 | 12/1978 | Iovine et al. | 260/17.46 C |
| 4,144,326 | 3/1979 | Luedicke, Jr. | 424/362 X |
| 4,155,885 | 5/1979 | Racciato et al. | 260/17.4 ST |
| 4,285,973 | 8/1981 | Edwards | 424/361 |

FOREIGN PATENT DOCUMENTS

| 2036453 | 12/1970 | France | 424/361 |
|---|---|---|---|
| 55-36412 | 3/1980 | Japan | 424/361 |
| 55-45602 | 3/1980 | Japan | 424/361 |

OTHER PUBLICATIONS

Research Disclosure No. 131 3/75, Union Carbide Corp., New York, N.Y., "Aqueous Cosmetic Cream Composition".

Primary Examiner—Dale R. Ore
Attorney, Agent, or Firm—Bucknam and Archer

[57] ABSTRACT

Copolymers of formula I are described

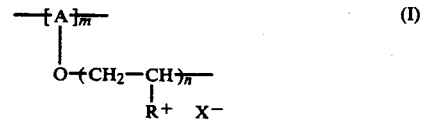

in which A is the monomeric unit of a natural or synthetic polymer, m is the degree of polymerization; m and n are different one from the other, and m is a number between about 300 and about 10,000 and n is a number between about 100 and about 250; R is a quaternary ammonium radical; $X^-$ is an anion. A may be the monomeric unit of starch or the monomeric unit of hydroxyethylcellulose. The substances exhibit substantial activity in the treatment of infections of the skin and mucosa and fungus infections and in general, high bactericidal activity accompanied by low toxicity.

2 Claims, No Drawings

COPOLYMERS HAVING BACTERICIDAL ACTIVITY, PROCESS FOR THE PREPARATION THEREOF AND PHARMACEUTICAL COMPOSITIONS THEREFROM

This application is a continuation-in-part of Ser. No. 201,297 filed Oct. 27, 1980, now abandoned.

The present invention relates to copolymers and more specifically to copolymers of formula (I),

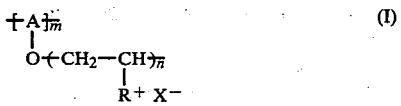

in which A is the monomer unit of a natural or synthetic polymer with degree of polymerization m;

m and n which, in general, are different one from the other, are numbers between 300 and about 10,000 in the case of m and between about 100 and about 250 in the case of n;

R is a quaternary ammonium radical, preferably one of the following formulae hereinbelow:

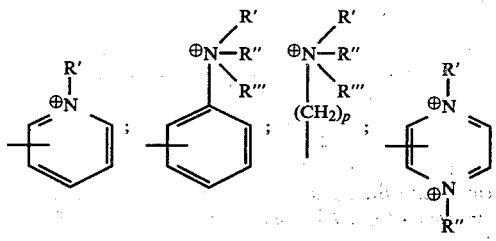

in which R′, R″, R‴, which may be the same or different one from the other, are alkyl or benzyl radicals and p is an integral number between 0 and 10;

$X^-$ is the anion from an inorganic or organic acid, preferably $Cl^-$, $Br^-$, $I^-$, $F^-$, $HSO_4^-$.

Compounds of formula I unexpectedly have exhibited high bactericidal activity accompanied by a very low toxicity.

It is well known that disinfectants and antiseptics ordinarily called surface active agents which contain quaternary ammonium groups exhibit high bactericidal activity against both gram-positive and gram-negative organisms, as well as against funguses and viruses. The toxicity of these compounds varies from one product to the other: however, it is certain that the administration by the oral, rectal or vaginal route may cause serious damages particularly if the administration had been made erroneously. Particularly, when these substances are administered orally, they cause nausea and vomiting, and after they are absorbed by the body, they may produce muscular paralysis because of the possibility of blockage of the respiratory muscles with the result that asphyxia follows.

The lethal dose of the most common quaternary surface active agents such as benzethonium chloride, benzylkonium chloride, methylbenzethonium chloride, cetylpyridinium chloride, has been estimated to be about 1-3 grams. The symptoms of poisoning are gastrointestinal irritation, dyspnea, cyanosis, collapse, convulsions, a state of dizziness, muscular weakness and finally death due to paralysis of the respiratory muscles.

In the concentrations used on the human skin, the solutions of the quaternary ammonium bases do not produce irritation but in some patients which are hypersensitive and after protracted use, they may produce phenomena of irritation and/or allergic reactions.

It has now been found surprisingly that the compounds of formula I in addition to exhibiting a very high activity, are also substantially devoid of toxicity both by the oral route and by application onto the skin as well as mucosae.

The synthesis of the products of the present application is carried out by means of a reaction of copolymerization which may be either ionic or of the free radical type by means of suitable initiators. The reaction of copolymerization may be carried out using as starting materials different monomeric units, thus obtaining copolymers which may be block copolymers or with an alternating or sequential arrangement. It is also possible to use as a starting material a pre-prepared polymer and then attach to it polymeric chain of different molecular weight of another functional monomer.

The monomeric unit which imparts to the product the chain

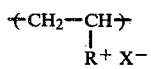

may also be in the form of a quaternary salt and the quaternization may be carried out prior to the reaction of copolymerization or after the reaction of copolymerization.

One object of the present application is to provide the novel copolymers of formula I hereinabove.

Another object is to provide a process for the preparation of the copolymers of formula I which involves grafting nitrogenous monomeric units, preferably 4-vinylpyridine onto oligosaccharides, polysaccharides, cellulosic derivatives, polyvinyl alcohol, etc.

The reaction of grafting is carried out by means of initiators for the purpose of forming suitable free radicals at a temperature lower than 40° C. For this reason, it is preferable to use redox initiator systems among which it is possible to mention the systems $Fe^{++}/H_2O_2$; $R-SH/H_2O_2$; $Na_2S_2O_3/H_2O_2$; $Ce^{4+}$ in solution of sulfuric or nitric acid, metallic salts of transition metals such as $V^{5+}$ and other similar salts.

Obviously, the products which are obtained depend upon the conditions used in the copolymerization reaction and specifically depend upon the quantity of the initiator used, the quantity of the monomer, the temperature and the reaction medium. It is, therefore, possible to obtain different quantities of synthetic polymers produced by an addition reaction with different molecular weight of the vinylpyridine chains which are grafted onto them. In general, the quantity of the polymer which is grafted varies between 10 to 60%, while the molecular weight is between 10,000 and 200,000.

The quantity of the polymer which is grafted may be determined on the basis of the increase in weight of a known amount of oligosaccharide and polysaccharide after the reaction of copolymerization as soon as the homopolymer such as polyvinylpyridine has been eliminated by means of a selective extraction with a suitable solvent or by means of elementary analysis of the nitrogen which is contained in a known quantity in the copolymer.

The reaction of quaternization of the copolymer may be carried out using different alkylating agents such as ethyl bromide, propyl bromide, butyl bromide, etc., cetyl chloride, benzyl chloride, etc., in a variety of solvents.

The polyvinylpyridine, either as such or copolymerized, is difficult to quaternize and the rate of quaternization decreases as the reaction proceeds. The choice of the reaction medium in which the reaction is carried out and the choice of the alkylating agent determine the extent of quaternization which may be achieved. Solvents having a high dielectric constant such as nitrobenzene, dimethylformamide, tetrahydrofuran, sulfolane, propylene carbonate have been found to be very suitable.

The quaternization reaction may be followed spectrophotometrically by infrared analysis during the course of reaction. Polyvinylpyridine exhibits a clear absorption band at 1600 cm$^{-1}$. As soon as the reaction of quaternization proceeds, a new band at 1640 cm$^{-1}$ appears. The degree of quaternization is calculated on the basis of the results of elementary analysis and the amount of halogen ions and other negative ions.

The final products exhibit a degree of quaternization between 60 and 95%.

The following non-limitative examples are given by way of illustration of the invention.

EXAMPLE 1

(a) Natural maize starch, in the amount of 5 grams is dissolved in 50 ml of boiling water. To the solution, there is added concentrated nitric acid in such a manner as to obtain a concentration of 1.5N, with respect to the acid. The mixture is deaerated to remove air for 10–20 minutes by passing nitrogen or argon through; then 10 ml of 4-vinylpyridine is added and subsequently a solution of cerium ammonium nitrate in nitric acid, so that the reaction system has a 0.01M concentration with respect to Ce$^{4+}$. The reaction mixture is stirred for 12 hours at room temperature; then 400 ml of a mixture of 10% sodium hydroxide and 1,2-propandiol, in the ratio of 3:1 are added. The precipitate which is formed is centrifuged and washed with distilled water until the starch disappears in the washing water. Subsequently, the material is washed with methanol in order to eliminate the 4-polyvinylpyridine which has not been grafted onto the starch matrix. The product after filtering exhibits an infrared spectrum in KBr with the following characteristic bands: 1600 cm$^{-1}$, 1220 cm$^{-1}$, 1070 cm$^{-1}$ and 820 cm$^{-1}$. The elementary analysis has given the following values: C=52.78%; H=4.82%; N=7.34%.

(b) The copolymer obtained as described in Example 1 in the amount of 7 grams, is suspended in 50 ml of methanol and treated with 10 grams of ethyl bromide. The reaction mixture is warmed under reflux for 120 hours, then the solvent and the excessive agent are evaporated up to a volume of about 15–20 ml. The material is then cooled to 0° C. and the resulting quaternary salt which is formed is filtered.

I.R. KBr: 1600 cm$^{-1}$ band has disappeared and the 1640 cm$^{-1}$ band is now present. The band is characteristic of quaternized pyridine.

Analysis: Br=39.80%

The product which is obtained is designated hereinbelow for short with the symbol FCB 1010.

EXAMPLE 2

(a) Twenty grams of hydroxyethylcellulose of average molecular weight 40,000 are dissolved in 350 ml of water. To the solution there is added 20 grams of concentrated nitric acid and then after deaeration by means of nitrogen, 30 ml of 4-vinylpyridine followed by a solution of cerium ammonium nitrate in nitric acid in such a quantity to achieve a concentration of Ce$^{4+}$ of 0.01M.

The reaction mixture is maintained under stirring for a period of 24 hours at 25° C. and then 1000 ml of 10% sodium hydroxide are added. The precipitate which is formed, is filtered, washed with water and then with methanol.

I.R. KBr: 1600 cm$^{-1}$, 1200 cm$^{-1}$, 1045 cm$^{-1}$, 830 cm$^{-1}$.

Analysis: C=42.46%; H=5.76%; N=3.05%.

(b) The copolymer described in Example 2a, in the amount of 15 grams, is dissolved in 75 grams of nitrobenzene and quaternized in 25 grams of ethyl bromide at 100° C. for a period of 48 hours. After the reaction is completed, the material is diluted with pentane and the quaternary salt which is formed is filtered and washed with a small amount of methanol.

I.R.: The 1600 cm$^{-1}$ band has disappeared and the 1640 cm$^{-1}$ band is now present.

Analysis: Br=16.54%.

The material which is obtained will be referred to hereinbelow with the symbol FCB 1011.

Microbiological Testing of the Antibacterial Activity of the Compounds FCB 1010 and FCB 1011

(1) Antibacterial activity as a function of the concentration of the products.

The products in the form of a whitish powder are dissolved in saline phosphate buffer prepared according to Sorensen of pH 7.2 in a concentration of 10% weight/volume which corresponds to 100 mg/ml.

For the purpose of testing the antibacterial activity of the products, 6 bacterial stocks purified by plaque clonation derived from human pathogenic germs maintained in the phase of logarithmic growth are used.

In particular, there are used in the following organisms:

(1) Gram—:
 *Escherichia Coli* (E.Coli)
 *Pseudomonas Aeruginosa* (Ps.Aer.)
 *Proteus Vulgaris* (Pr.Vulg.)
(2) Gram+:
 *Micrococcus Luteus* (M. Lut.)
 *Streptococcus Fecalis* (S. Fec.)
 *Staphylococcus Aureus* (S. Aur.)

A liquid medium with ample spectrum of capacity of growth is used as the culture medium, that is Bactotryptic Soy Broth (Difco).

The activity of the products is determined using the concentrations of 0.1%, 0.01% and 0.001% in a liquid culture medium both for FCB 1010 and FCB 1011. For comparison purposes, there is used α-(p-tolyl)dodecyltrimethylammonium methoxysulfate in the same concentrations.

For each dilution of the product there are utilized four test tubes each containing 20 ml of the liquid medium.

The antibacterial activity is determined by the turbidometric test after 24 hours of incubation at 37° C. The test consists of determining the values of reduction of the light transmitted from the culture media which contain the microorganisms under test and the products in different concentrations using as a control the same media together with the pharmaceutical substance being tested in the same concentration. The values are expressed in percentage of the cultures without addition of any antibacterial substance. For each test, there are used $7.5 \times 10^5$ live gram-negative bacteria and $9.2 \times 10^5$ live gram-positive bacteria.

Results:

In Table 1 hereinbelow are reported the effects of FCB 1010 in different concentrations with respect to the organism under test. It is possible to observe that the product FCB 1010 in the concentrations of 0.1% and 0.01% inhibits totally the growth of all bacteria tested. In the concentration of 0.001%, the substance exhibits an antibacterial activity, particularly with respect to *Escherichia Coli, Pseudomonas Aeruginosa* and *Micrococcus Luteus*.

In Table 2 hereinbelow, the antibacterial activity exhibited by the substance FCB 1011 is shown. Also, this substance prevents the antibacterial growth with all the organisms which have been studied up to a concentration of 0.01%, while in the concentration of 0.001%, the activity decreases substantially, but the inhibitory effect of 50–60% is maintained.

The effect of α-(p-tolyl)-dodecyltrimethylammonium methoxysulfate (Desogen), are tabulated in Table 3. They are substantially inferior with respect to the two preceding products. In fact, in the concentration of 0.01%, this substance does not prevent bacterial growth with any of the organisms tested.

TABLE 1

Antibacterial activity of the Product FCB 1010 at different concentrations with respect to several bacteria under test

| Test No. | Conc. of the Substance | E. Coli | Ps. Aer. | Pr. Vul. | M. Lut. | S. Fec. | S. Aur. |
|---|---|---|---|---|---|---|---|
| 1 | — | 100% | 100% | 100% | 100% | 100% | 100% |
| 2 | 0.1% | 0% | 0% | 0% | 0% | 0% | 0% |
| 3 | 0.01% | 0% | 0% | 0% | 0% | 0% | 0% |
| 4 | 0.001% | 51% | 42.2% | 76.31% | 55% | 63% | 64% |

TABLE 2

Antibacterial activity of the Product FCB 1011 at different concentrations with respect to several bacteria under test

| Test No. | Conc. of the Substance | E. Coli | Ps. Aer. | Pr. Vul. | M. Lut. | S. Fec. | S. Aur. |
|---|---|---|---|---|---|---|---|
| 1 | — | 100% | 100% | 100% | 100% | 100% | 100% |
| 2 | 0.1% | 0% | 0% | 0% | 0% | 0% | 0% |
| 3 | 0.01% | 0% | 0% | 0% | 0% | 0% | 0% |
| 4 | 0.001% | 59% | 44.3% | 66.4% | 61.3% | 58% | 61% |

TABLE 3

Activity of the Product Desogen at different concentrations with respect to the bacteria under test

| Test No. | Conc. of the Substance | E. Coli | Ps. Aer. | Pr. Vul. | M. Lut. | S. Fec. | S. Aur. |
|---|---|---|---|---|---|---|---|
| 1 | — | 100% | 100% | 100% | 100% | 100% | 100% |
| 2 | 0.1% | 0% | 0% | 0% | 0% | 0% | 0% |
| 3 | 0.01% | 18% | 27% | 39% | 16% | 26% | 21% |
| 4 | 0.001% | 78% | 66% | 72% | 86% | 84% | 83% |

(2) Antibacterial activity as a function of the concentrations of the products and their contact times with the bacteria.

The antibacterial activity as a function of the contact time of the surface active agents with the bacteria has also been investigated. The bacteria are suspended in water; FCB 1010, FCB 1011 and α-(p-tolyl)-dodecyltrimethylammonium methoxysulfate have been used in concentration of 0.1% and 0.01%. After 2, 5, 15 minutes of contact time, a sample of 0.1 ml has been placed into a medium of liquid culture as described hereinabove for a period of 48 hours. Each test according to the different times and different concentrations has been carried out four times. The medium for the evaluation of the bacterial growth was the same as the method previously described. However, the results are expressed in a semi-quantitative manner in order to provide a better evaluation of the effective antibacterial activity (turbidimetric values of 1–30%+++; 30–60%++; 60–90%+). The results so obtained are reported in Table 4 hereinbelow using different contact times of the product with respect to the organisms with the two concentrations which have been studied.

It is evident that the products FCB 1010 and 1011 are active as antibacterial agents against all the organisms tested in the concentrations of 0.1% and 0.01% even after only two minutes of contact time.

The product used as a comparison exhibits an activity in the same order of magnitude against all bacteria except *Pseudomonas Aeruginosa* because in the case of this organism, the substance at the concentration of 0.01% does not exhibit a total bactericidal action.

TABLE 4

| Substances Tested | C. % | T.C. | E. Coli | Ps. Aer. | Pr. Vulg. | M. Lut. | S. Fec. | S. Aur. |
|---|---|---|---|---|---|---|---|---|
| FCB 1010 | 0.1 | 2 | — | — | — | — | — | — |
|  |  | 5 | — | — | — | — | — | — |
|  |  | 15 | — | — | — | — | — | — |
|  | 0.01 | 2 | — | — | — | — | — | — |
|  |  | 5 | — | — | — | — | — | — |
| FCB 1011 | 0.1 | 2 | — | — | — | — | — | — |
|  |  | 5 | — | — | — | — | — | — |
|  |  | 15 | — | — | — | — | — | — |
|  | 0.01 | 2 | — | — | — | — | — | — |
|  |  | 5 | — | — | — | — | — | — |
|  |  | 15 | — | — | — | — | — | — |
| DESOGEN | 0.1 | 2 | — | — | — | — | — | — |

TABLE 4-continued

| Substances Tested | C. % | T.C. | E. Coli | Ps. Aer. | Pr. Vulg. | M. Lut. | S. Fec. | S. Aur. |
|---|---|---|---|---|---|---|---|---|
| | | 5 | — | — | — | — | — | — |
| | | 15 | — | — | — | — | — | — |
| | 0.01 | 2 | — | + | — | — | — | + |
| | | 5 | — | + | — | — | — | |
| | | 15 | — | + | — | — | — | — |

Disinfectant and antimycotic activity in "vivo"

(a) The disinfectant activity in "vivo" has been studied in 40 patients affected by dermatosis of infective nature, generally pyogenic such as pyodermia, streptodermia, staphylodermia, acne, and in general inflamed prominent elevations of the skin. FCB 1010 and FCB 1011 have been applied on the skin of 20 patients both in the concentration of 1%, two or three times a day up to an improvement of the clinical condition. The therapeutic effect has been found to be optimum in 80% of the patients treated both in the case of FCB 1010 and FCB 1011. In addition, none of the treated patients exhibited any reactions of cutaneous intolerance nor did any of the patients exhibit any reactions of allergic nature.

(b) The antimycotic activity in "vivo" was determined with 30 patients affected by superficial cutaneous mycosis of different types both from the morphologic-clinical point of view as well as stage, caused by a variety of different funguses. Also, in this case, FCB 1010 and FCB 1011 were applied onto the skin in a concentration of 1%, two or three times a day to 15 patients up to an improvement of the clinical condition. This improvement was achieved very substantially in 86% of the individuals with FCB 1010 and 80% with FCB 1011.

During treatment, no secondary reactions, either at the cutaneous level or in general, were noted.

Allergological Tests

The allergological tests have been carried out with 60 individuals who had an allergic dermatosis and who had, therefore, high cutaneous activity, by application onto the skin.

FCB 1010 and FCB 1011 have been applied three times a day in different concentrations on an equal number of sections of the skin for a period of 30 days. The concentrations of the products selected for the test have been 4%, 2% and 1%. None of the patients manifested any symptoms of cutaneous intolerance connected with the treatment.

CLINICAL TRIALS OF THE PRODUCTS FCB 1010 AND FCB 1011

The products FCB 1010 and FCB 1011 have been tested in the therapy of the following diseases: acne with foruncolosis, sycosis barbae, acute ulcerative gengivitis, moniliasis, ringworm of the feet, ferite torpide.

TREATMENT OF ACNE WITH FORUNCOLOSIS BY MEANS OF FCB 1010 AND FCB 1011

Sixty patients affected by juvenile acne with foruncolosis in the face who had not responded to conventional anti-bacterial treatments used either topically or by general route have been treated with the two substances according to the present invention. Thirty patients have been treated with FCB 1010 and 30 patients with FCB 1011 by applying a lotion three times daily, the lotion containing the active substance in different concentration. The 60 patients have been divided in groups of 10 patients each and the treatments with the active substance have been carried out in the same conditions of dosage but under difference concentrations, 0.5%, 1% and 2%. In the group treated with FCB 1010 at 0.5% concentration, after a week of treatment, four patients have shown a cure, that is disappearance of the foruncolosis and two patients have shown improvement, that is reduced extent of foruncolosis. In the case of the other patients, it has not been possible to see a change in the cutaneous infective condition.

The patients who had shown improvement or the patients who had not shown any visible change have been treated with FCB 1010 for another week in the concentration of 2% and at the end of the period of treatment, all the patients have shown almost a total disappearance of the foruncolosis.

Eight of the patients treated with FCB 1010 in the concentration of 1% have shown a cure after a seven-day period of treatment while all the patients treated with a lotion of 2% concentration have exhibited a cure, in the course of one week.

With respect to the patients treated with FCB 1011 in the concentration of 0.5%, five patients have shown an improvement while the others have shown no change. The treatment has been continued for seven more days with a 2% lotion of FCB 1011 and eight of them have been cured while the others have shown a substantial improvement. With respect to the group of patients treated with FCB 1011 in the concentration of 1%, seven of them have shown a cure while two of them have only shown an improvement and in one patient the foruncolosis has shown essentially no change. With the administration of a 2% lotion of FCB 1011, a cure has been obtained in eight patients and an improvement in the other two. The local and general tolerance to the substances in the different concentrations used has been observed with all the subjects treated.

TREATMENT OF SYCOSIS BARBAE WITH FCB 1010 AND FCB 1011

Twenty patients affected by sycosis barbae have been treated with FCB 1010 and FCB 1011 with lotions containing 0.5% and 1% of the substances. The patients have been divided in groups of five subjects who have used three times daily a lotion containing respectively 0.5% and 1% of FCB 1010 and 0.5% and 1% of FCB 1011. All the subjects treated have shown a cure in the course of a week of treatment without showing any side effect attributable to the treatments.

TREATMENT OF ACUTE ULCERATIVE GENGIVITIS

Forty patients affected by acute ulcerative gengivitis have been treated by rinsing the mouth with an aqueous solution containing 1% and 2% of the active ingredient. The rinsing has been carried out six times daily in 20 patients with the lower concentration, 10 with FCB 1010 and 10 with FCB 1011 and the other 20 patients with the higher concentration. All the patients in the course of seven days of treatment have been cured or have shown a substantial improvement of the pain symptoms of the disease and the ulcerative lesions in the oral cavity have disappeared. No substantial therapeutical difference has been shown between the two concentrations and the two products. The tolerance to the treatments has been optimum in all the patients and no local side effects in general have been noted.

TREATMENT WITH FCB 1010 AND FCB 1011 OF MONILIASIS OF THE ORAL CAVITY AND THE VAGINAL CAVITY

Twenty patients affected by moniliasis of the oral cavity have been treated by rinsing and by brushing eight times daily for a period of seven days with FCB 1010 and FCB 1011 with solutions containing the active ingredient in the concentration of 2%. Ten patients treated with FCB 1011 have shown optimum results, that is cure in eight patients and improvement in the other two, while the patients treated with FCB 1011 have shown less dramatic results, that is four patients have been cured and two have shown an improvement.

Twenty-seven women affected by moniliasis of the vaginal cavity have been treated with the active ingredient in the concentration of 2% in the form of a vaginal douche and with two small amounts of solid material containing 100 mg. each of FCB 1010 and FCB 1011 daily. After five days of treatment, it has been possible to observe that all the women treated with FCB 1010, that is 14 patients as well as the 13 patients treated with FCB 1011 have been cured. Treatment has not caused side effects of any kind, both locally as well as in the general system.

TREATMENT WITH FCB 1010 AND FCB 1011 OF RINGWORM OF THE FEET

Sixty patients affected by ringworm of the feet have been treated with FCB 1010 and FCB 1011 for a period of 10 days. The products, according to the present application, are the only drugs specifically used against this fungus infection, and therefore, they have been used in association with the conventional hygienic and therapeutical practices which ordinarily accompany the treatment of this disease.

All the patients have bathed in a solution containing 2% of the material twice daily, 30 patients with FCB 1010 and 30 patients with FCB 1011, and then they are treated with a powder containing 5% of the active material. At the end of the treatment, it has been possible to establish that in 54 patients, the fungus infection had been cured and only in six patients the fungus infection was still present essentially to the same extent. Four of these patients had been treated with FCB 1011 and two with FCB 1010. These patients subsequently have been treated for a period of 10 days increasing the number of baths and the number of local administration of the powder. At the end of the second period of treatment, only two patients treated with FCB 1011 still had not been cured.

TREATMENT WITH FCB 1010 AND FCB 1011 OF CUTANEOUS ULCERS IN PHLEBOTHROMBOSIS

Forty patients affected by torpid ulcers in the lower extremeties due to venous phlebothrombosis have been treated with FCB 1010 and FCB 1011. The patients have had the ulcers for a long time, which ulcers had been accompanied by a bacterial infection in places which had already been treated with conventional agents which promote cicatrization. These patients have been subjected to a treatment twice daily letting a solution of 1% concentration and 2% concentration of FCB 1010 and FCB 1011 drop on the ulcer, drop by drop, during a period of two hours. After manually drying the wound, a thin layer of powder of one of the two substances sufficient to well cover the wound has been applied. The treatment has been continued for 20 days in the same manner, 10 patients being treated with a solution containing 1% of FCB 1010 and 10 patients being treated with FCB 1011 of the same concentration while the other 20 patients have been treated with FCB 1010 and FCB 1011 with a solution of double concentration. All the patients treated with FCB 1011 have shown a substantial improvement with an increase of the granular tissue, cleansing of the ulcer and re-epithelialization of the same with complete cure in 16 patients. The patients treated with FCB 1010 have exhibited less dramatic results with cicatrization occurring only in nine patients and substantial improvement in five other patients. The remaining six patients have been subjected to a therapeutical cycle with FCB 1011 and they have shown substantial improvement with total cure in five of them at the end of the second therapeutical cycle. None of the patients has shown any side effects attributable to the drugs.

OVERALL EVALUATION OF THE THERAPEUTICAL ACTIVITY OF FCB 1010 AND FCB 1011

Table 4 hereinbelow reports the number of patients treated in each case of disease, the therapeutical activity, the dose per day, the length of the treatment and the manner of use of the substances. It is clearly noteworthy that FCB 1010 and FCB 1011 exhibit optimum activity on a number of infective agents of the skin and mucosae, which are difficult to treat with conventional medicinals used topically. In fact, the two substances are active on infections due to Staphylococcus (that is acne with foruncolosis and sycosis barbae), fusospirochetal (acute ulcerative gengivitis), canadida albicans (moniliasis), fungus infections in general (ringworm of the feet), bacterial flora in general (cutaneous ulcers). The substances, FCB 1010 and FCB 1011, therefore, exhibit a bacterial and fungicidal activity of great importance in the therapy of skin infections in humans. The active doses are totally devoid of side effects because the substances are not absorbed through the skin and mucosae. Due to their molecular weight and due to their structure, they may easily adhere to hair and skin exhibiting a continuous action with time.

TABLE 5

| DIAGNOSIS | NO. OF PATIENTS | CURED | IMPROVED | NO CHANGE | DOSE PER DAY | LENGTH OF TREATMENT | SUBSTANCE USED | |
|---|---|---|---|---|---|---|---|---|
| Acne With | 10 | 4 | 2 | 4* | 3 Appl. | 7 | Solution: FCB 1010 | 0.5% |
| Foruncolosis | 10 | 9 | — | 1* | 3 Appl. | 7 | FCB 1010 | 1% |
| | 10 | 10 | — | — | 3 Appl. | 7 | FCB 1010 | 2% |
| | 10 | 5 | — | 5 | 3 Appl. | 7 | FCB 1011 | 0.5% |

TABLE 5-continued

| DIAGNOSIS | NO. OF PATIENTS | CURED | IMPROVED | NO CHANGE | DOSE PER DAY | LENGTH OF TREATMENT | SUBSTANCE USED | |
|---|---|---|---|---|---|---|---|---|
| | 10 | 7 | 2 | 1 | 3 Appl. | 7 | FCB 1011 | 1% |
| | 10 | 8 | 2 | — | 3 Appl. | 7 | FCB 1011 | 2% |
| Sycosis Barbae | 5 | 5 | — | — | 3 Appl. | 7 | FCB 1010 | 0.5% |
| | 5 | 5 | — | — | 3 Appl. | 7 | FCB 1010 | 1% |
| | 5 | 5 | — | — | 3 Appl. | 7 | FCB 1011 | 0.5% |
| | 5 | 5 | — | — | 3 Appl. | 7 | FCB 1011 | 1% |
| Acute Ulcerative Gengivitis | 10 | 10 | — | — | 6 Appl. | 7 | FCB 1010 | 1% |
| | 10 | 10 | — | — | 6 Appl. | 7 | FCB 1010 | 2% |
| | 10 | 10 | — | — | 6 Appl. | 7 | FCB 1011 | 1% |
| | 10 | 10 | — | — | 6 Appl. | 7 | FCB 1011 | 2% |
| Moniliasis | 10 | 8 | 2 | — | 8 Appl. | 7 | FCB 1010 | 2% |
| | 10 | 4 | 2 | 4 | 8 Appl. | 7 | FCB 1011 | 2% |
| | 14 | 14 | — | — | 2 Appl. | 5 | FCB 1010 +2 solid egg-shaped material of 100 mg. | 2% |
| | 13 | 13 | — | — | 2 Appl. | 5 | FCB 1011 +2 solid egg shaped material of 100 mg. | 2% |
| Ringworm of the Feet | 30 | 28 | — | 2* | { 2 Appl. | 10 | FCB 1010 | 2% |
| | | | | | 2 Appl. | | Powder FCB 1010 | 5% |
| | 30 | 26 | — | 4* | { 2 Appl. | 10 | FCB 1011 | 2% |
| | | | | | 2 Appl. | | Powder FCB 1011 | 5% |
| Cutaneous Ulcers | 10 | 4 | 2 | 4 | { 2 Appl. | 20 | Solution FCB 1010 | 1% |
| | | | | | 2 Appl. | | Powder FCB 1010 | |
| | 10 | 5 | 3 | 2 | { 2 Appl. | 20 | Solution FCB 1010 | 2% |
| | | | | | 2 Appl. | | Powder FCB 1010 | |
| | 10 | 8 | 2 | — | { 2 Appl. | 20 | Solution FCB 1011 | 1% |
| | | | | | 2 Appl. | | Powder FCB 1011 | |
| | 10 | 9 | 1 | — | { 2 Appl. | 20 | Solution FCB 1011 | 2% |
| | | | | | 2 Appl. | | Powder FCB 1011 | |

*repeated treatment

Toxicity Tests

FCB 1010 and FCB 1011 have been administered orally to Swiss rats and Spraque-Dawley rats in order to determine the acute toxicity, that is $DL_{50}$. The $DL_{50}$ has been found in both species to be greater than 3 g/kg. Another test has been carried out to determine the toxicity over an extended period of time with Beagle dogs for a period of four months. The tests have shown that with a daily dose of 1 or 2 g/kg, no change attributable to the products FCB 1010 and FCB 1011 has been found.

Another object of the invention is the preparation of pharmaceutical compositions for topical use, such as creams, ointments, lotions, etc., having antibacterial and antimycotic activity which contain as the active principle at least one of the copolymers of formula I, together with carriers and excipients conventionally used in the formulations of a pharmaceutical compositions.

Still another object of the invention resides in the method of treatment of patients affected by dermatosis of infective nature, such as pyodermia, streptodermia, staphylodermia, acne and cutaneous mycosis by means of the compounds of formula I. Clearly, the invention covers all the operations required for the preparation of the copolymers, their purification, their formulation in pharmaceutical forms suitable for the administration and/or the final confection in containers suitable for the administration.

What is claimed is:

1. The method of treatment of a patient affected by infections of the skin of the type of pyrodermia, streptodermia, staphylodermia, acne, cutaneous mycosis, moniliasis, ulcerative gingivitis, sycosis barbae and ringworm of the feet; which consists of applying to the area of the patient affected by said infections of the skin a composition containing 0.1–5% of a compound of formula I

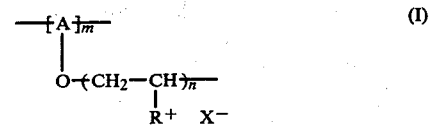

wherein A is the starch or hydroxyethylcellulose unit, m is the degree of polymerization;
  m and n are different one from the other, and m is a number between about 300 and about 10,000 and n is a number between about 100 and about 250;
  R is a quaternary ammonium radical which is a member selected from the group consisting of formulae (a), (b), (c) and (d)

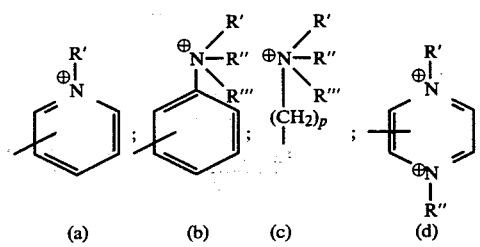

in which R', R", R''', are the same or are different one from the other and are alkyl or benzyl radicals and p is an integral number between 0 and 10;

X⁻ is the anion Cl⁻, Br⁻, I⁻, F⁻ or HSO₄⁻; together with conventional carriers or excipients for creams, ointments, lotions and powders.

2. The method, according to claim 1, wherein A is maize starch or hydroxyethylcellulose and R is

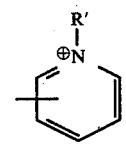

wherein R' is ethyl.

* * * * *